United States Patent
Siegel et al.

(10) Patent No.: US 8,450,692 B2
(45) Date of Patent: May 28, 2013

(54) INCREASING EDGE SENSITIVITY IN A RADIATION DETECTOR

(75) Inventors: Stefan B. Siegel, Knoxville, TN (US); Dongming Hu, Knoxville, TN (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 148 days.

(21) Appl. No.: 13/101,367

(22) Filed: May 5, 2011

(65) Prior Publication Data

US 2011/0272587 A1    Nov. 10, 2011

Related U.S. Application Data

(60) Provisional application No. 61/331,414, filed on May 5, 2010.

(51) Int. Cl.
*G01T 1/20* (2006.01)

(52) U.S. Cl.
USPC .............. 250/362; 250/370.09; 250/370.1; 250/366

(58) Field of Classification Search
USPC ......... 250/362, 366, 370.11, 370.09, 370.1; 356/310
See application file for complete search history.

(56) References Cited

U.S. PATENT DOCUMENTS

| | | | |
|---|---|---|---|
| 4,437,160 A * | 3/1984 | Blum | 250/369 |
| 5,015,861 A * | 5/1991 | Derenzo et al. | 250/361 R |
| 8,183,531 B2 * | 5/2012 | Chinn et al. | 250/363.04 |
| 2006/0202125 A1* | 9/2006 | Suhami | 250/368 |
| 2010/0108894 A1* | 5/2010 | Pratx et al. | 250/362 |
| 2010/0148075 A1* | 6/2010 | Chinn et al. | 250/362 |
| 2010/0301221 A1* | 12/2010 | Nakamura | 250/366 |
| 2011/0127434 A1* | 6/2011 | Wollenweber | 250/362 |
| 2012/0061576 A1* | 3/2012 | Degenhardt et al. | 250/362 |
| 2012/0138804 A1* | 6/2012 | Miyaoka et al. | 250/362 |

* cited by examiner

*Primary Examiner* — David Porta
*Assistant Examiner* — Taeho Jo
(74) *Attorney, Agent, or Firm* — Peter Kendall

(57) ABSTRACT

An apparatus and method to increase the sensitivity at the edge of radiation detector blocks is disclosed herein. Reduced sensitivity can result from photons entering a first detector block, escaping, and scattering into an adjacent detector, thereby depositing energy into two detectors blocks. Energy lost into adjacent detector blocks can be compensated with energy detected in the adjacent detector block. This can be done, for example, by processing channels from multiple detector blocks with one Field Programmable Gated Array (FPGA) on one Event Process Module (EPM) board. This can enable summing energy of one detector block with energy from an adjacent detector block when the initial interaction occurs at the edge of the first detector block. This can result in a better estimate of the amount of energy associated with the initial photon being detected.

15 Claims, 11 Drawing Sheets

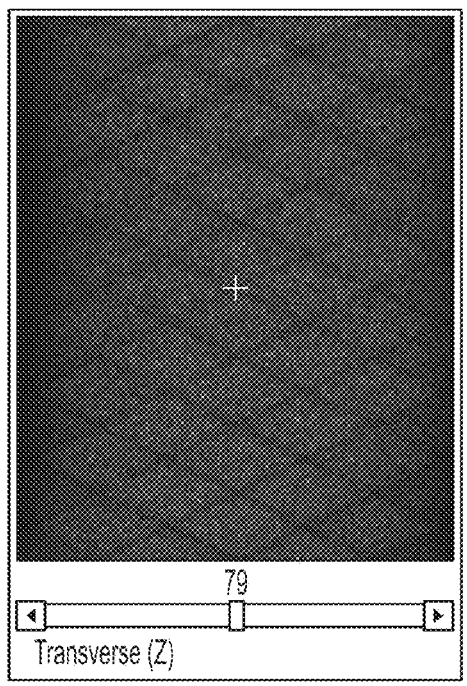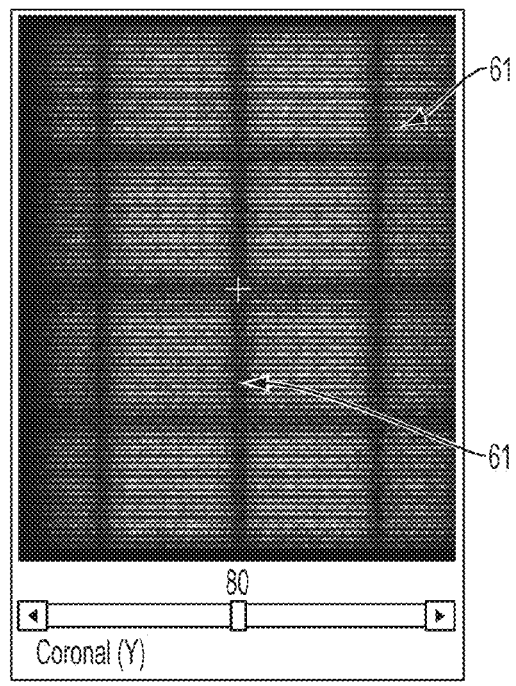
FIG. 6a
(Prior Art)
FIG. 6b
(Prior Art)
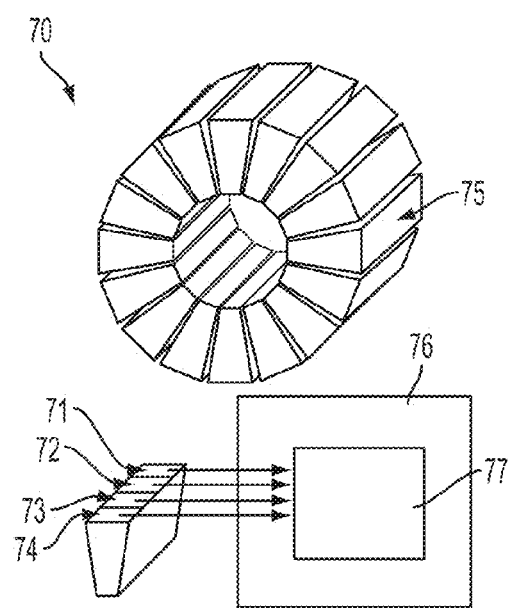
FIG. 7

INCREASING EDGE SENSITIVITY IN A RADIATION DETECTOR

CROSS-REFERENCE TO RELATED APPLICATIONS

This is a non-provisional patent application of pending U.S. provisional patent application Ser. No. 61/331,414, filed May 5, 2010, by Stefan Siegel and Dongming Hu, titled "Increasing Edge Sensitivity of Modular PET Detectors by Incorporating Information from Adjacent Detectors", the entirety of which application is incorporated by reference herein.

TECHNICAL FIELD

The present invention concerns signal acquisition in radiation detectors in such fields as nuclear imaging detectors, e.g., Positron Emission Tomography (PET) or Single Photon Emission Tomography (SPECT).

BACKGROUND

In the field of nuclear medical imaging technology, a subject, e.g. an oncology patient or an animal used in an experiment, can be scanned by detecting radiation emanating from the subject. For example, in a so-called PET scan, a short-lived radioisotope, which decays by emitting a positron, is injected usually into the blood circulation of a living subject. After the metabolically active molecule becomes concentrated in tissues of interest, the research subject or patient is placed in the imaging scanner. The most commonly-used metabolically active molecule for this purpose is 18F-fluorodeoxyglucose (FDG), a sugar, which has a half life of 110 minutes.

As the radioisotope undergoes positron emission decay, it emits a positron, the antimatter counterpart of an electron. After traveling up to a few millimeters, the positron encounters and annihilates with an electron, producing a pair of gamma photons moving in almost opposite directions. These are detected when they reach one of a plurality of scintillation crystals in the scanning device, creating a burst of light detected by an array of photosensors.

Radiation emanating from the subject can be detected in, for example, radiation detector ring assembly 13 illustrated in FIG. 1. At a more granular level, specific radiation events can be detected at detector block 16 comprising an array of radiation sensors, such as plurality of scintillators and associated photosensors $11_n$, such as photomultiplier tubes (PMTs), avalanche photodiodes (APDs), or silicon photomultipliers (SiPMs). In the case of a PET scan, scintillators can be arranged in a ring 13.

Generally a plurality of sensors, e.g., photosensors 11, can be arranged in a matrix and assigned to detect the light of a single scintillator as shown in detector block 16 in FIG. 1. Detector block 16 can be associated with a single scintillation crystal 13 or can be, as shown, a matrix of scintillator crystals that is coupled to the photosensors 11 1 . . . 11n usually via a light guide. A plurality of detector blocks 16 can be axially arranged adjacent to one another, in a slot, in a line relative to the center of ring 13. To be able to increase the resolution of the system without the high costs of 1:1 coupling, the number of photosensors 11 per block is generally significantly lower than the number of scintillation crystals 13. For example, a detector block may have a plurality of radiation sensors, such as photosensors 11 with, for example, 4, 9 or 16 photosensors 11 arranged in a 2×2, 3×3, or 4×4 matrix behind an array of scintillation crystals 13. Other arrangements with more or fewer photosensors 11 are possible. Thus, scintillation event localization can be determined or interpolated by such a detector block by processing the associated photosensor signals. This can be done by analog filtering, integration, and multiplication of weighted combinations of the photosensor signals or by using digital algorithms that use discrete time sample points of signals obtained directly from the photosensors 11. The PET technique depends on scintillation event detection of the pair of gamma photons.

FIG. 1 illustrates a block diagram of the typical architecture of a detector block 16 and associated analog-to-digital-converters $14$-$14_n$ in a conventional system. Each matrix of photosensors 11 produces a plurality of signals that can be processed to generate an image from a plurality of scintillation events that are detected by a photosensor 11. To determine the location of a detected annihilation, the system needs to accurately measure the timing and energy of both detected photons. Consequently a high amount of data has to be produced by the respective measurement circuits.

For example, as shown on the right side of FIG. 1, each scintillator has an associated matrix of detector blocks, such as photosensors $11_1$ . . . $11_n$, which, in this example are PMTs. Each signal of each PMT $11_1$ . . . $11_n$ is first amplified by, for example, associated preamplifiers/buffers $12_1$ . . . $12_n$. The output signal of preamplifier/buffers $12_1$ . . . $12_n$ can then be converted concurrently into discrete-time digital signals by associated analog-to-digital converters (ADC) $14_1$ . . . $14_n$. A sampling clock for each ADC be can provided at terminal 15. In this example, this digital processing architecture uses n independent ADC signals with peripheral circuitry to concurrently sample each of n photosensor signals per block. This can increase the costs of a detector block.

FIG. 2 illustrates a detector block 20 comprising an 8×8 array of scintillation crystals; for example, each crystal can be 4 mm×4 mm×20 mm. Photosensors 11 can be included behind the scintillation crystals to detect light emitted due to scintillation events.

Not all radiation emanating from a subject is detected by scanner 10. Radiation can be emitted outside of the field of view of scanner 10, or radiation can scatter. For example, Compton scatter, which can occur when a photon collides with an electron, thereby transferring energy to the electron. The collision can cause the photon to deviate from its original path and cause a loss of energy. This collision typically occurs within the subject or in, for example, a scintillation crystal. Due to Compton scattering, events that would otherwise have been detected may be missed.

The probability that a 511 keV gamma ray be detected is a function of the material composition of the detector block, its size, and its density. For LSO, the probability that the first interaction of the 511 keV gamma ray is a Compton scatter is on the order of 68%, and for short, narrow pixels, the fraction of Compton scatter exiting the pixel can be quite significant.

SUMMARY

In a detector block where the Compton scattered gamma photon can be subsequently absorbed in an adjacent pixel, the positioning of the event can be weighted by the distribution of deposited energy between the two points of interaction, and the total energy can be calculated using the sum of this deposited energy.

The impact of the Compton scatter on sensitivity is noticeable at the edges of the detector block, as there is no adjacent pixel on one or two sides of the pixels. In this situation, the contribution of the Compton scattered gamma to the total energy detected is lost, and events fail to satisfy the energy window constraint. This loss in overall system sensitivity is exacerbated in PET as the detector slots are run in coincidence, and the efficiency drops as the product of the individual detector block efficiency losses.

Multiple interactions (e.g., Compton scattering and photoelectric absorption) of 511 keV gamma-rays in PET scanners results in multiple energy depositions. If the multiple energy depositions of the scattered gammas occur in one detector block, the energy sum will still be correctly detected, although the location of the first point of interaction is blurred. However, if the multiple energy depositions happen on the edge of two adjacent detector blocks, neither block will reflect the energy of the incident gamma-ray correctly. In this case, the event might be rejected on the basis of energy discrimination, which yields effectively lower sensitivities at the edge crystals of PET scanners.

Embodiments of the present disclosure include an apparatus and method to increase the low sensitivity at the edge of detector blocks, such as PET block detectors. Compton scattering often can result in part of the incident photons energy escaping from a first detector block, and thereby depositing energy in a second detector block, effectively reducing the sensitivity of the first detector block. To solve the problem of low sensitivity in the edge of the detector block, lost energy can be compensated for with the energy detected in adjacent detector blocks. This can be done, for example, by processing channels from multiple detector blocks with one Field Programmable Gated Array (FPGA) on one Event Process Module (EPM) board. This can enable summing energy from adjacent detector blocks when an edge crystal detects an event. Illustrative results show that the edge crystal sensitivity of a PET detector block comprised of a 20×20 element LSO array with 1.5×1.5×10 $mm^3$ pixels can increase by, for example, more than 10% in singles detection. The sensitivity of a system of such detector blocks can increase by ~10% for coincidence detection between an edge pixel and an interior pixel, and ~21% for coincidence detection between edge pixels in two separate detector blocks.

A first exemplary embodiment includes a radiation detection device having sensors that are arranged to form detector blocks that are arranged to be adjacent to one another in a row. The radiation detection device further includes a processor configured to receive a first signal from a first detector block, and a second signal from a second detector block. The processor is also configured to correct the first signal using the second signal, wherein first detector block is adjacent to the second detector block.

A second exemplary embodiment includes a method of increasing detection of events at detector block boundaries. The method includes receiving first energy of a first photon at a first detector block that generates a first signal representing the first energy of the first photon. The method further includes receiving second energy of the first photon, which escaped the first detector, at a second detector block, which generates a second signal, from a second detector block, representing the second energy of the first photon. The method also corrects the first signal using the second signal to generate a corrected signal.

A third exemplary embodiment includes a method of increasing crystal efficiency, which includes receiving, from a first detector block, a first signal indicative of first energy of a photon. The method also includes receiving, from a second detector block, a second signal indicative of second energy of the photon. The method further includes sending the first signal and the second signal to an Event Processing Module (EPM), summing the first signal and the second signal to generate a corrected signal, and logging the corrected signal if the corrected signal is indicative of a photon having energy above a predetermined threshold.

BRIEF DESCRIPTION OF THE DRAWINGS

FIGS. 6a and 6b illustrate a sinogram of cylinder phantom acquired using a detector block of the prior art.

FIG. 7 illustrates a ring of detector slots and a detector slot with a corresponding event processing module (EPM).

DETAILED DESCRIPTION

Figure 1:
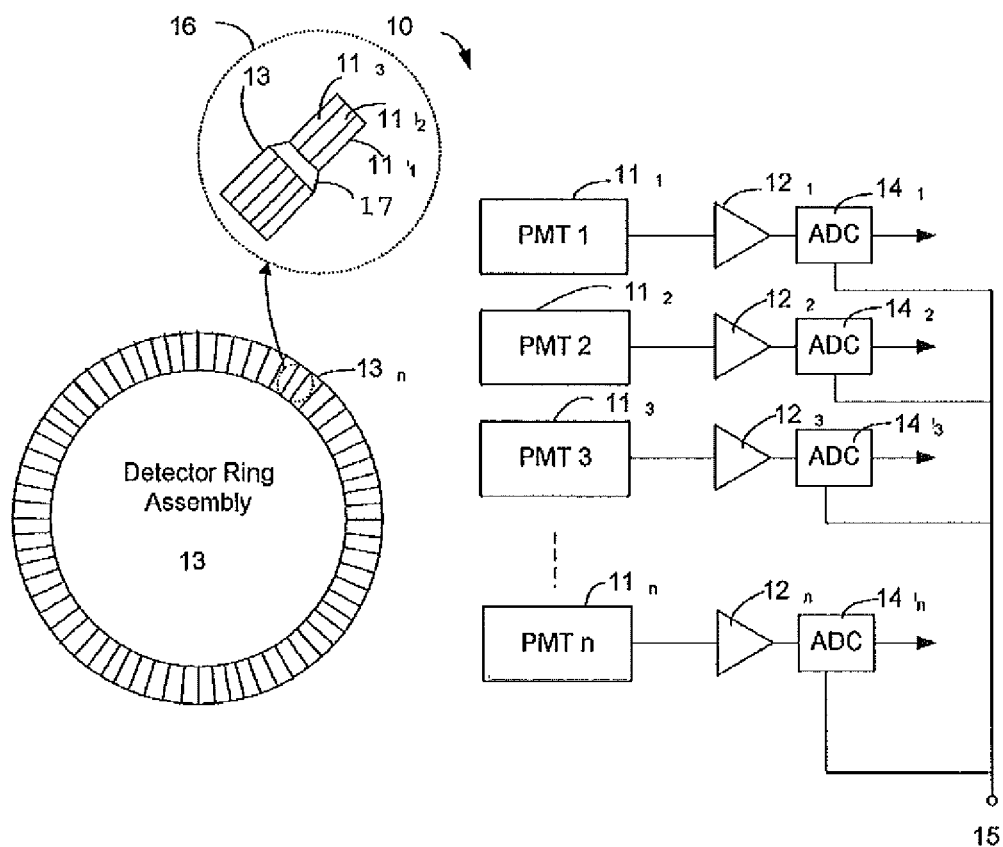
FIG. 1 illustrates a conventional detector ring assembly with associated detector circuitry of a conventional PET scanner.
Figure 2:
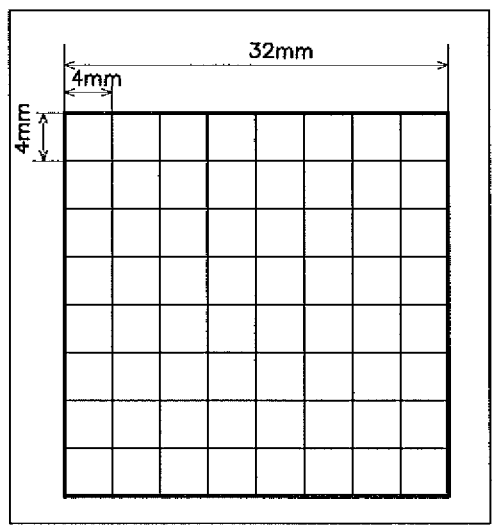
FIG. 2 illustrates an 8×8 array of scintillation crystals.
Figure 3:
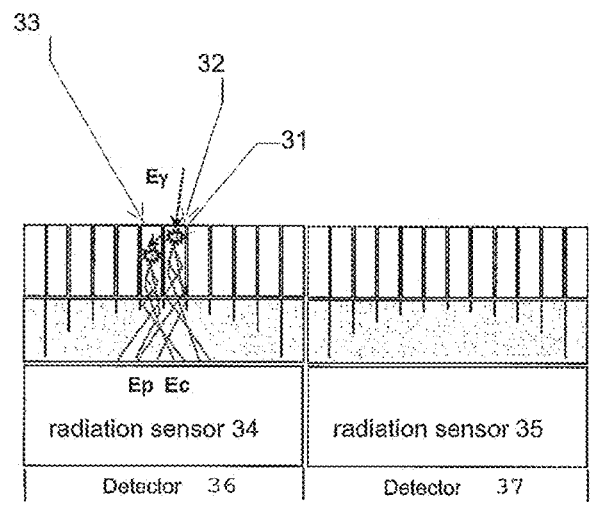
FIG. 3 illustrates multiple energy depositions of a gamma photon within scintillation crystals corresponding to one detector block.

Multiple interactions (e.g., Compton scattering and photoelectric absorption) of a gamma-ray photon with a PET scanner can result in energy being deposited in multiple locations. If the energy is deposited into multiple locations of the same detector block, the EPM can correctly sum the energy, although the XY position of the incident can be blurred. In other embodiments, energy can be received at different EPMs, and processed in a separate processor. As illustrated in FIG. 3, a gamma-ray photon 31 with energy Eγ is scattered in one crystal 32 and absorbed in another crystal 33. Since both Compton scattering and photoelectric absorption happen in the detector block 36, the energy Eγ=Ec+Ep can be detected by summing up Ec and Ep in detector 36 block.

Figure 4:
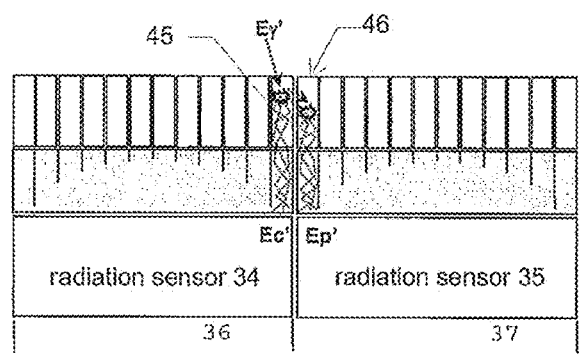
FIG. 4 illustrates multiple energy depositions of a gamma photon within scintillation crystals corresponding to adjacent detector blocks.
Figure 5:
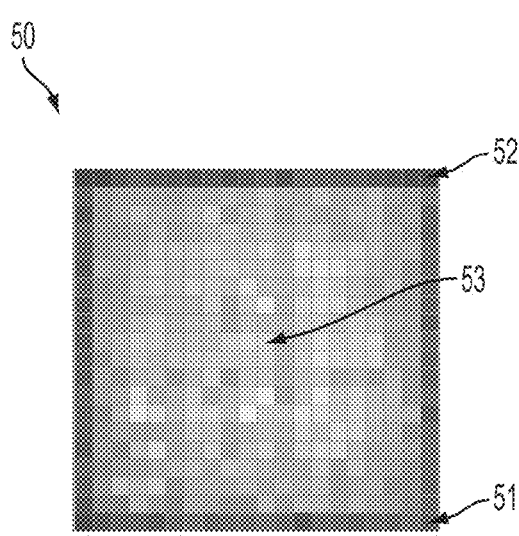
FIG. 5 illustrates the sensitivity of crystals in a detector block.

However, as illustrated in FIG. 4, for a photon with energy Eγ', entering scintillation crystal 45, if the scattering occurs in an edge crystal 45 of detector block 36 and photoelectric absorption also happens in edge crystal 46 of adjacent detector block 37, neither detector block may collect enough of energy Eγ' for either detector block to detect the event because they can be coupled to different radiation sensors 34 and 35 and processed in different channels, and therefore different EPMs. In other words, discriminators associated with each of the detector blocks may discard the event because neither Ec' nor Ep' has enough energy to register as a true event. Detector block 36 only receives energy of Ec' meanwhile detector block 37 only detects energy of Ep'. Since Eγ'=Ec'+Ep', the event is likely to be rejected later by energy discriminators in detector blocks 36 and 37, which results in low sensitivities in the edge crystals of detector blocks. The low sensitivity of the edge crystals of detector blocks can be observed in the crystal image and sinogram as shown in FIG. 5. The reduced sensitivity can be due to photons escaping to adjacent detector blocks, and therefore not registering as true events.

While the example just described illustrate discrete crystals, other applications include using one continuous crystal, which can be logically separated into virtual pixels for data processing, reconstruction, and final rendering to a user. Virtual pixels are portions of an analog signal that are separated into discrete portions for translation into a digital signal. The principles disclosed herein would be similar in that energy from adjacent integrated crystals can be summed to yield the total energy deposited by a photon.

FIG. 5 illustrates a crystal map of a detector block associated with a 20×20 array of crystals 50. The gray level of each crystal represents the coincidence count, i.e., efficiency of the crystal. Edge crystals 51 and 52 receive fewer counts and have less efficiency, and are therefore darker, than center crystals 53. This can be due to scattering of energy at the boundaries of the crystals. In other words, photons received at the edge of a crystal array may escape and dissipate energy in two different detector blocks, in which case, discriminators may assume that the energy is insufficient and ignore or drop the photon.

FIG. 6a illustrates a transverse view of a cylinder sinogram, and FIG. 6b illustrates a coronal view of the same cylinder sinogram. From the coronal view, it can be seen that the edges 61 of the four detector blocks in the same slot and the edges between the slots generate dark gaps in the sinogram.

FIG. 7 illustrates an exemplary detector ring 70 having LSO detector blocks, which can be packaged in 16 slots 75 arranged into a ring 70. Other arrangements are possible, for example, the detector blocks could be arranged in a ring, semi-circle or flat panel. In the example illustrated in FIG. 7, each slot can contain 4 detector blocks (71-74) that can be installed axially to the tunnel. Since there are 16 slots 75, the detector ring 70 will have a total of 64 LSO detector blocks. The detector blocks (71-74) can have 20×20 crystal matrices and be coupled to Position Sensitive PMTs (PSPMTs). The outputs signals of PSPMTs of detector blocks 71-74 on the same slot are fed to an EPM 76 board and digitally processed by a FPGA 77. This structure provides a path to use sum energy from axially adjacent blocks to correct event energy when an event occurs at a crystal on a trans-axial edge, and energy is dissipated into adjacent detector blocks. Processing signals from multiple detector blocks enables this summing because the signals are sent to the same destination or EPM.

Figure 8:
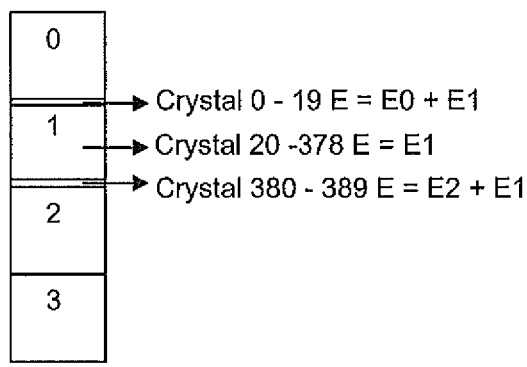
FIG. 8 illustrates how energy can be shared between crystals in adjacent detector blocks.

As shown in FIG. 7, detector blocks 71 and 73 are in the same slot 75 of detector ring 70 and are arranged adjacent to detector block 72. Discriminators associated with each of the detector blocks (71-74) will only pass on signals having energy greater than a predetermined threshold. EPM board 76 can collect energy from all detector blocks (71-74) when any of the discriminators for any of the detector blocks (71-74) are triggered. For example, when a photon enters detector block 1 as shown in FIG. 8, samples can also be taken in the adjacent detector blocks 0 and 2. In this manner, energy transferred to adjacent detector blocks due to scatter can be captured to correct the signal of detector block 1. A photon received at the center of detector block 1 can still cause detector blocks 0 and 2 to sample data; however, this behavior is of little concern because simultaneous events are rare and discarded if they do occur.

Figure 9:
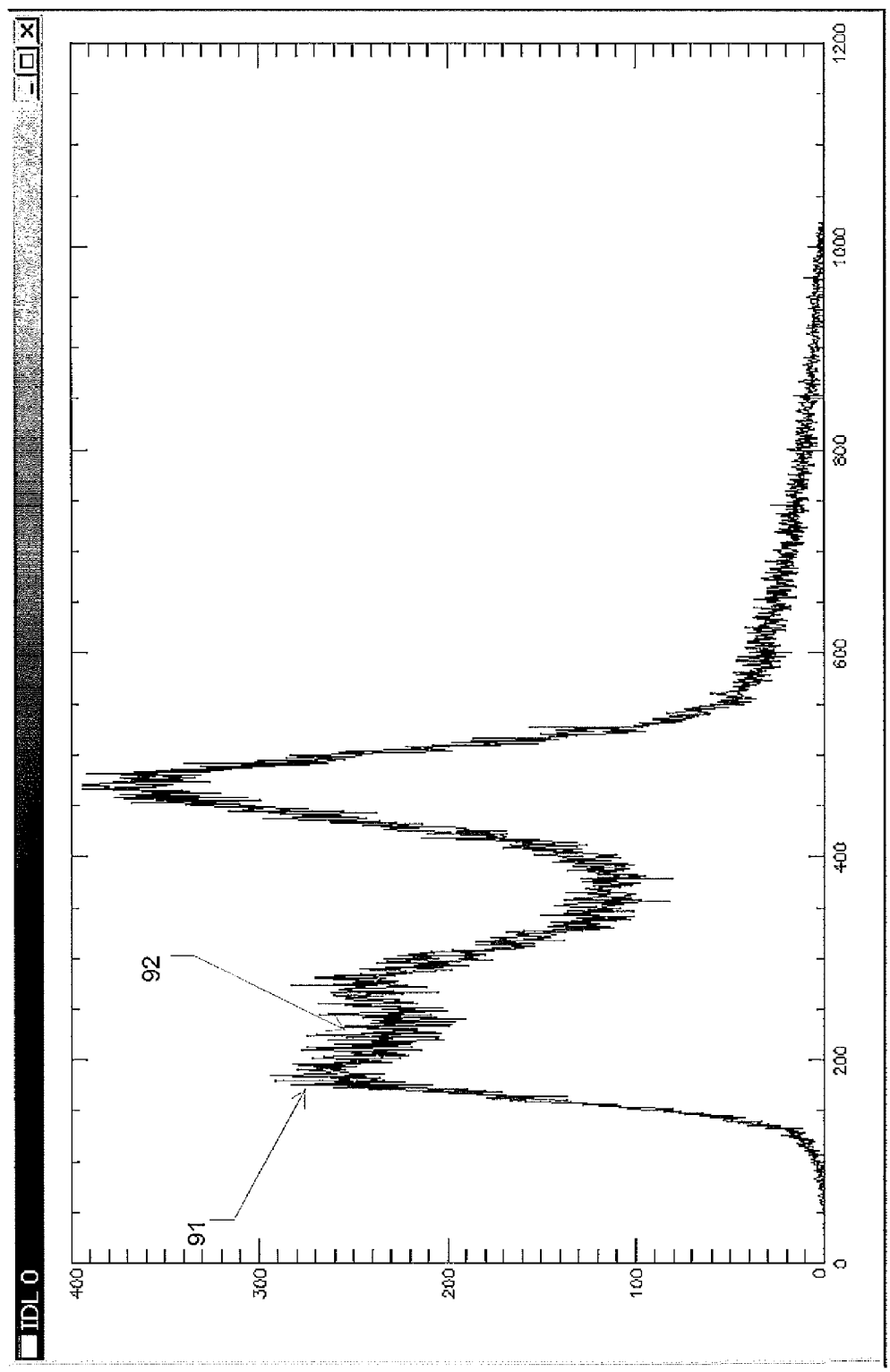
FIG. 9 illustrates energy spectra of an interior crystal with and without energy correction.
Figure 10:
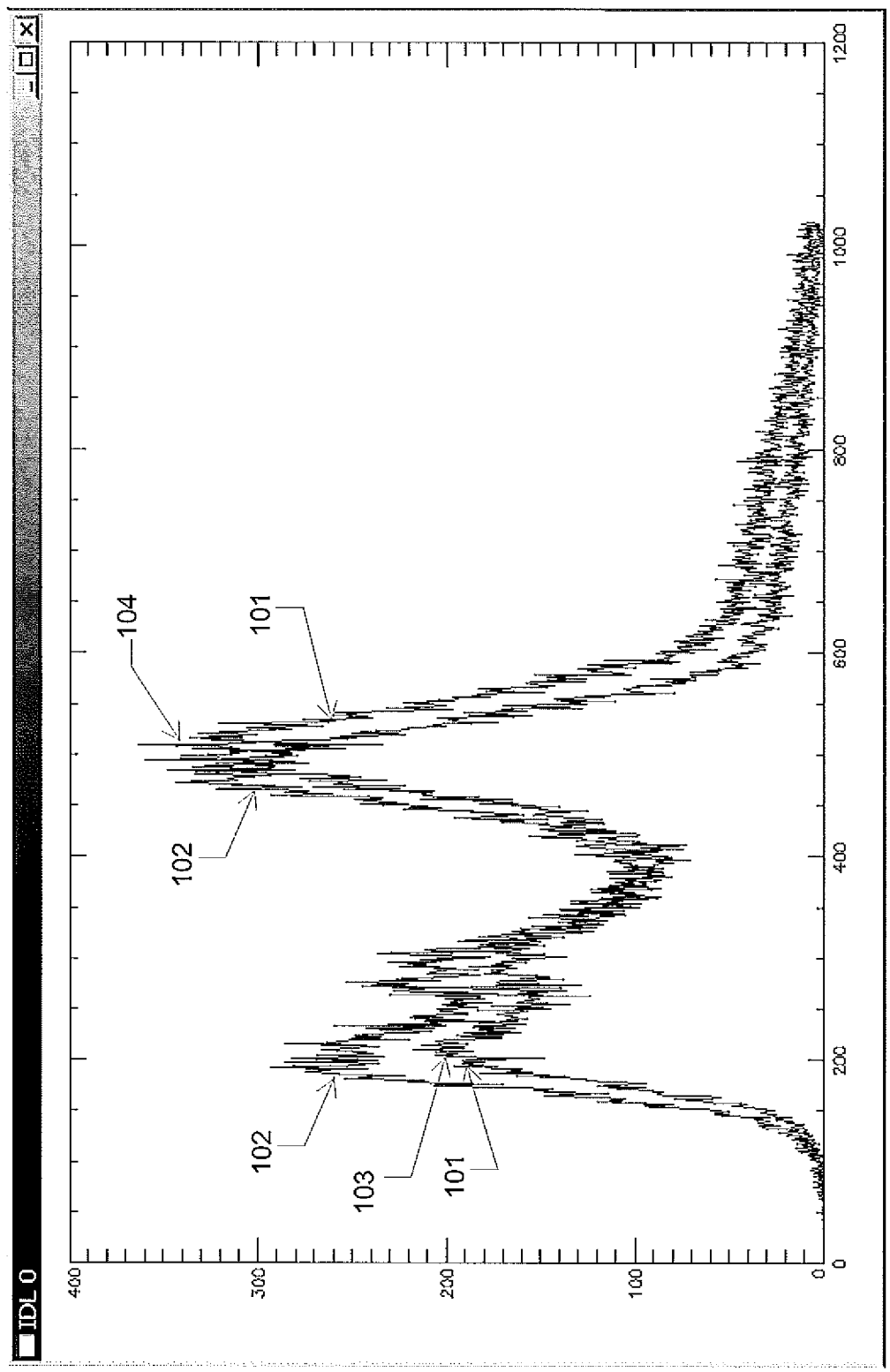
FIG. 10 illustrates energy spectra of an edge crystal with and without energy correction.
Figure 11:
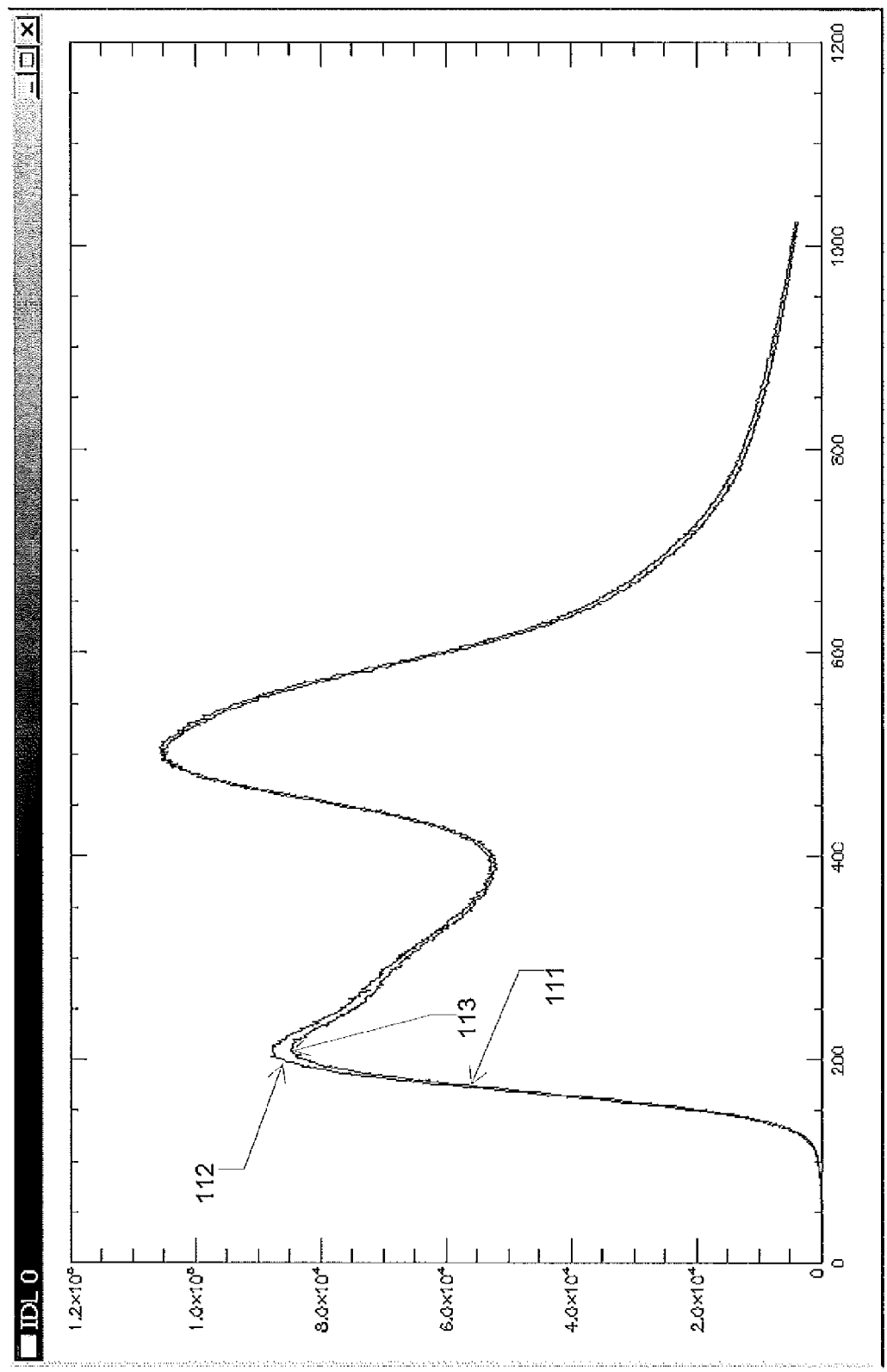
FIG. 11 illustrates the global energy spectra for a system comprised of a ring of 16 detector slots, with and without energy correction.

The crystal energy spectral of an exemplary detector block is illustrated in FIGS. 9 and 10. FIGS. 9 and 10 each plot energy spectrals (91 and 92; and 101 and 102, respectively), one for crystals with energy correction and one without. FIG. 9 illustrates energy spectrals 91 and 92 corresponding to internal crystals, for energy correction and without, respectively, spectrals 91 and 92 are substantially identical because substantially all energy received by internal crystals will be collected by the same detector block, so energy is not dissipated in adjacent detector blocks. Therefore, energy correction does not have much, if any, effect on center crystals. However, the contribution of energy correction for edge crystals is apparent in spectrals 101 and 102, illustrated in FIG. 10. Energy spectral 101, with energy correction, has a lower Compton plateau 103, because some singles in the energy range of Compton plateau 103 are corrected close to the photo peak 104, and the photo peak 104 is shifted to higher energy. This indicates that energy correction works properly. The overall effects of energy correction in the edge crystals can be further confirmed in the system's energy spectrum shown in FIG. 11, which illustrates spectral without energy correction 111, and with energy correction 112. Spectral 112, with energy correction, has a lower Compton plateau 113, corresponding to Compton plateau 103. As there are significantly fewer edge pixels than internal pixels, the overall change at the system level can be subtle.

Figure 12:
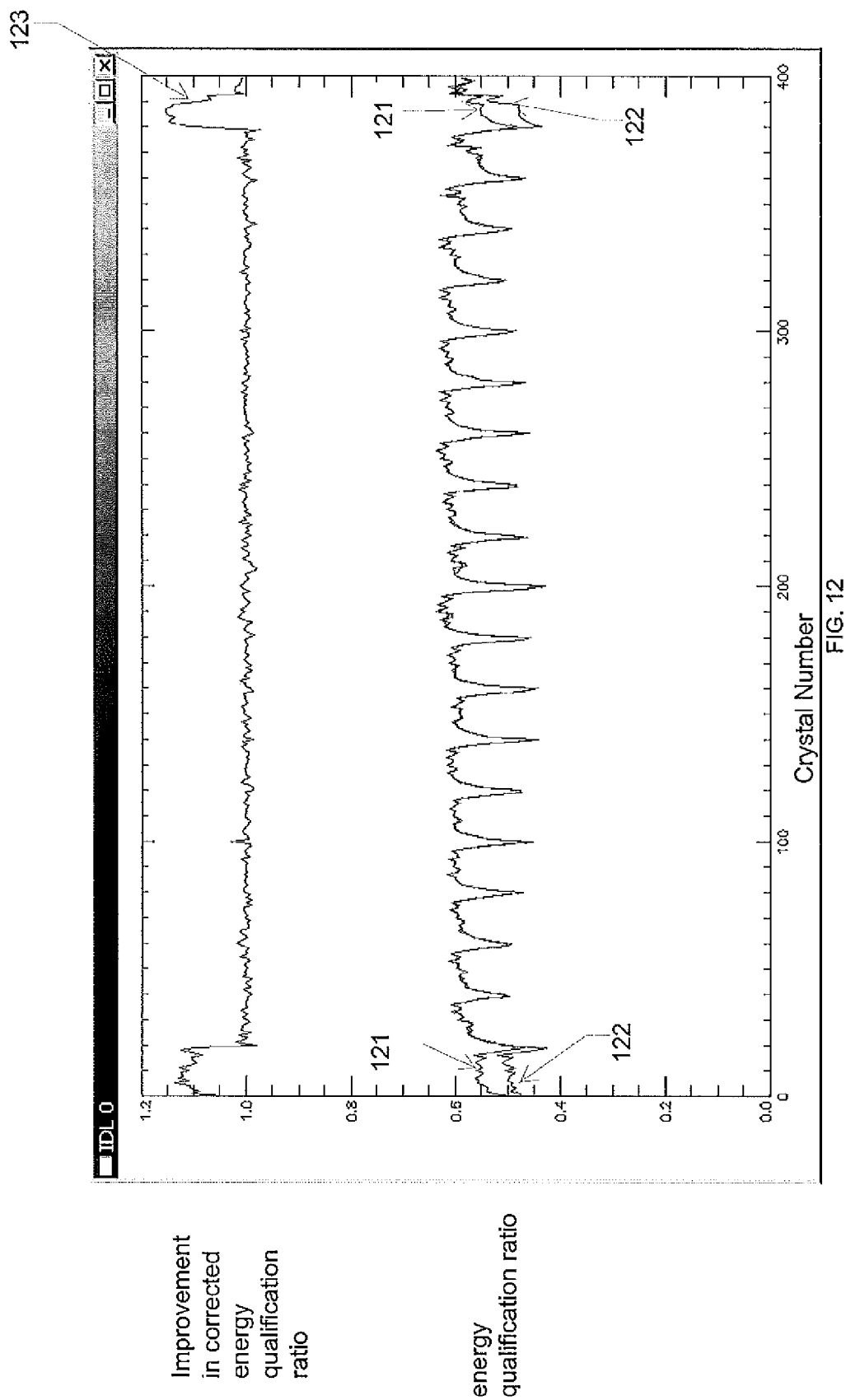
FIG. 12 illustrates a singles energy qualification ratio with and without energy correction.

We can define a singles energy qualification ratio as the total energy-qualified singles (i.e., true singles) vs. total singles (i.e., wide open energy window). In FIG. 12, the singles energy qualification ratio 121, with energy correction, and ratio 122, without energy correction, are plotted for illustration. For central crystals (20-378), ratio 121 substantially matches ratio 122. For the corrected edge (0-19 and 380-399), ratio 121 is much higher than ratio 122, which means the energy correction in the edge crystals recovers more energy-qualified singles. The ratio 123, which is (ratio 121):(ratio 122), is also plotted to quantitatively indicate the improvement in the singles energy qualification ratio using energy correction. For the internal crystals, the (ratio 121):(ratio 122) remains 1.0. For the edge crystals, (ratio 121):(ratio 122) has a mean value of 1.096, which indicates an average increase of 9.6% for energy-qualified singles. Since, in this example, 40 crystals on the two edges are corrected, which is 10% of the 400 crystals in a block, the improvement on the singles energy qualification ratio for the block is roughly 1%.

In an embodiment of the present disclosure used in a PET scanner, which identifies coincidence events, i.e., a pair of gamma-ray photons generated due to a positron annihilation, the increase in sensitivity is squared because two events must be identified to define a line of response. Therefore, the improvements described herein can be particularly beneficial when applied to PET and other coincidence-dependent applications.

Figure 13:
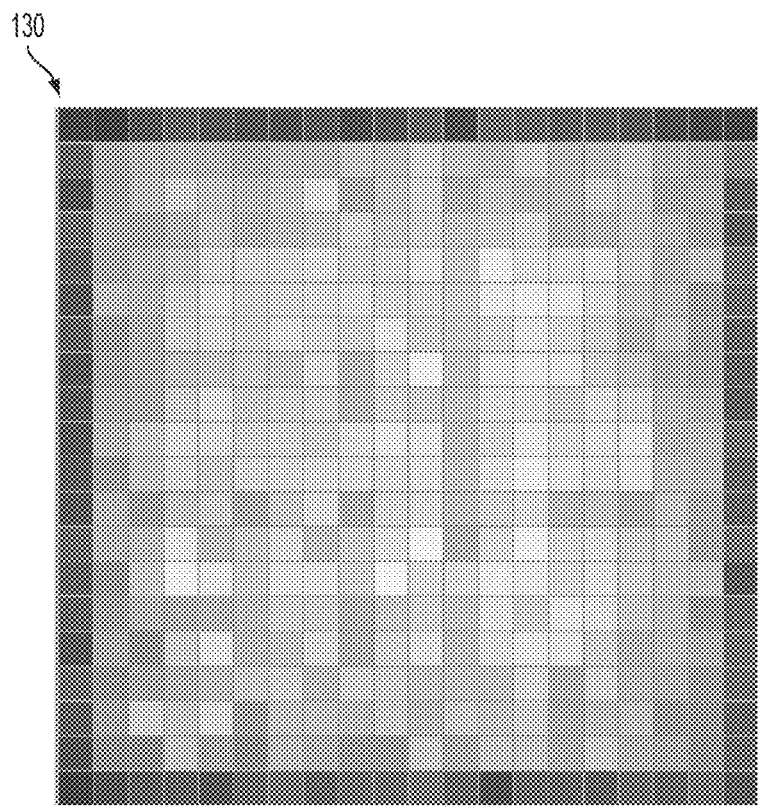
FIG. 13 illustrates uncorrected sensitivity of crystals in a detector block similar to FIG. 5.
Figure 14:
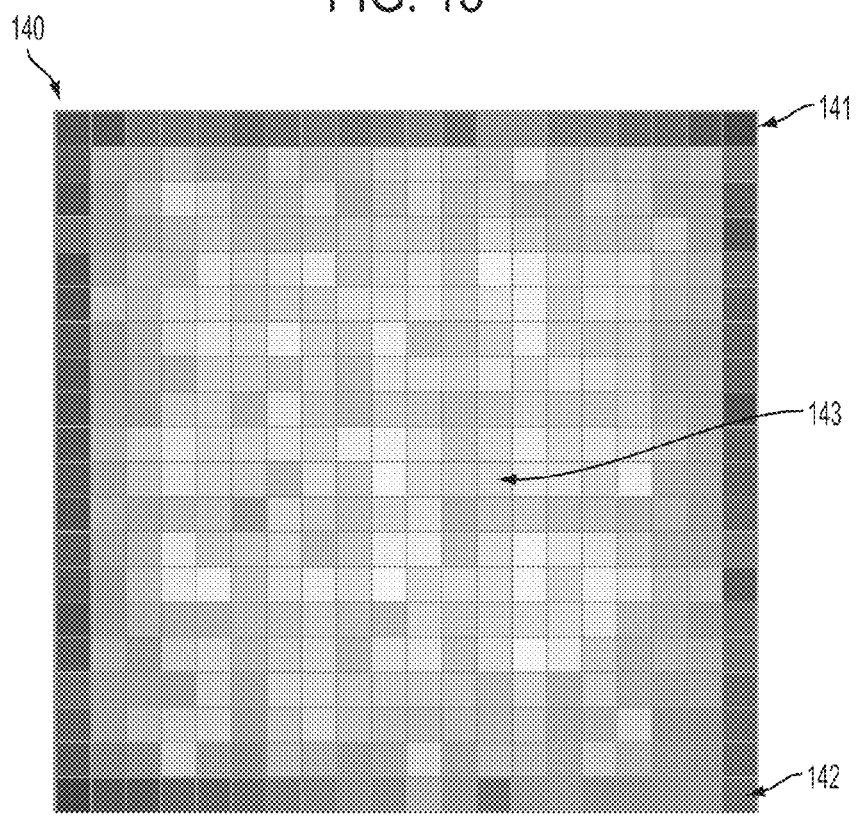
FIG. 14 illustrates corrected sensitivity of crystals in a detector block.

Another way to view the improvement in edge-crystal sensitivity is by comparing gray levels of crystal efficiency between an uncorrected detector block 130 of FIG. 13, and corrected detector block 140 FIG. 14. Compared to the uncorrected detector block 130, the gray levels of corrected crystals of detector block 140 in top edge 141 and bottom edge 142 are closer to the gray levels of the central crystals 143, i.e., the gray levels on edges 141 and 142 are lighter, which indicates greater crystal efficiency.

Figure 15:
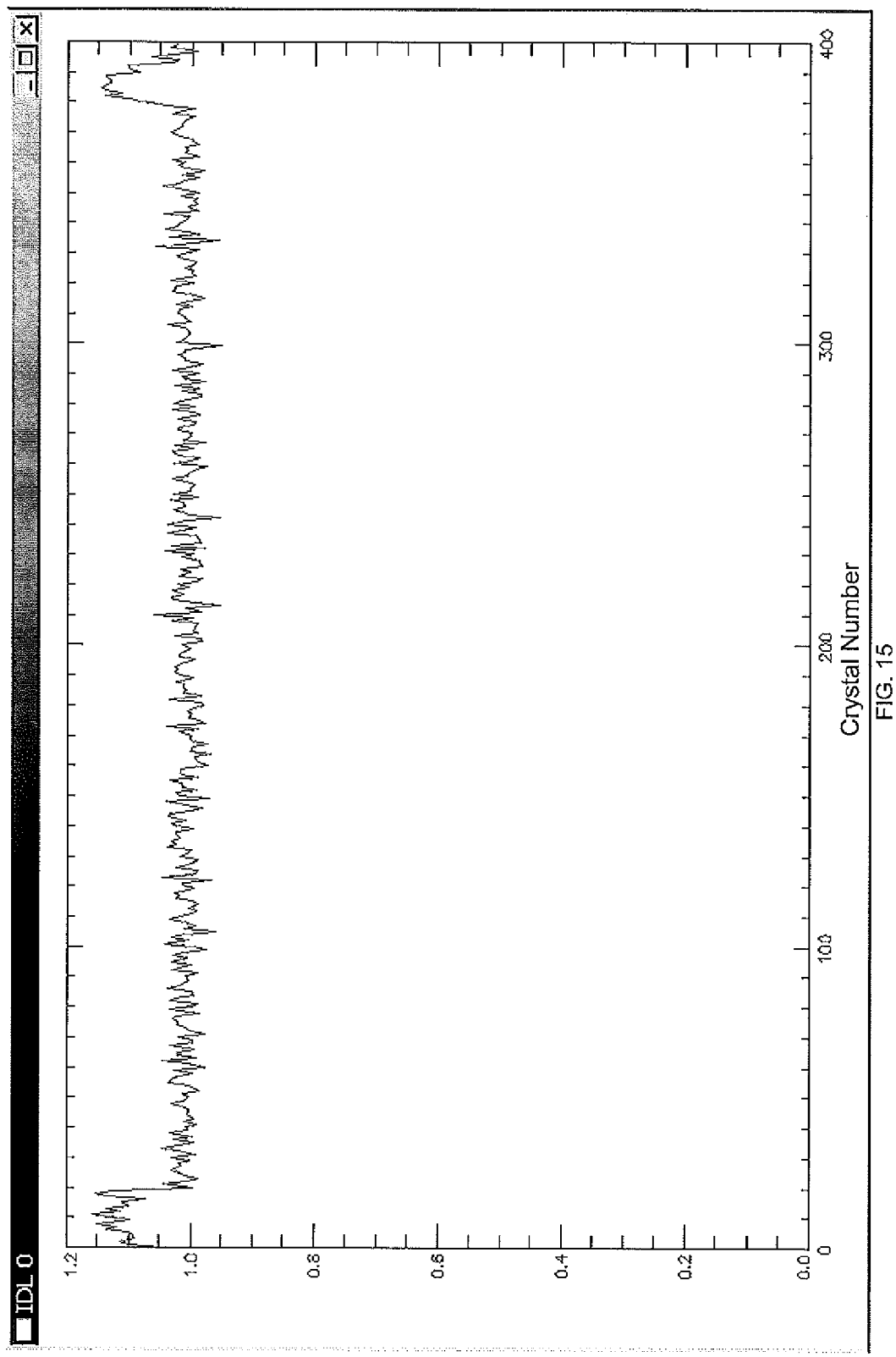
FIG. 15 illustrates a ratio of crystal efficiency of an exemplary detector block.

The ratio of corrected vs. uncorrected crystal efficiency is illustrated in the plot of FIG. 15. Since the opposite detector block has a similar detector block improvement of the singles energy qualification ratio, which can be about 10%, for example, we see a very similar curve to line 123 in FIG. 12. In this example, the average efficiency improvement is 10.1% for the corrected edge crystals and 1.8% for the block.

Figure 16:
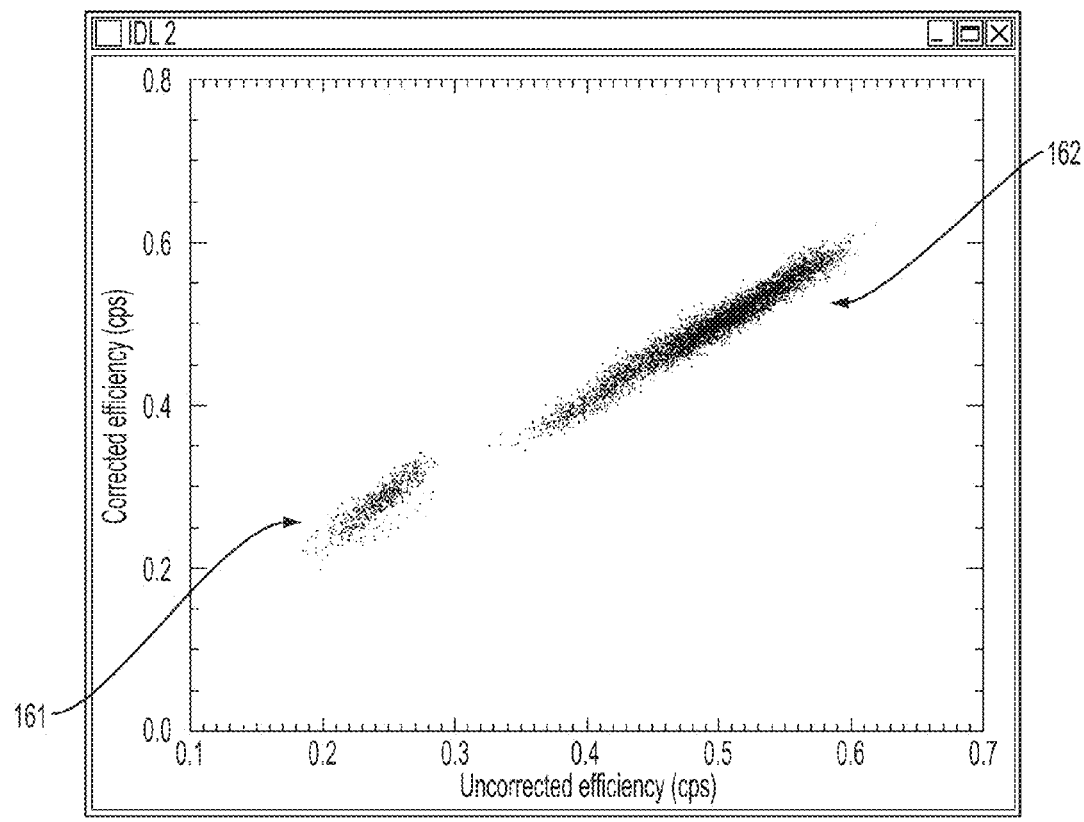
FIG. 16 illustrates the scatter plot of uncorrected vs. corrected crystal sensitivities.
Figure 17:
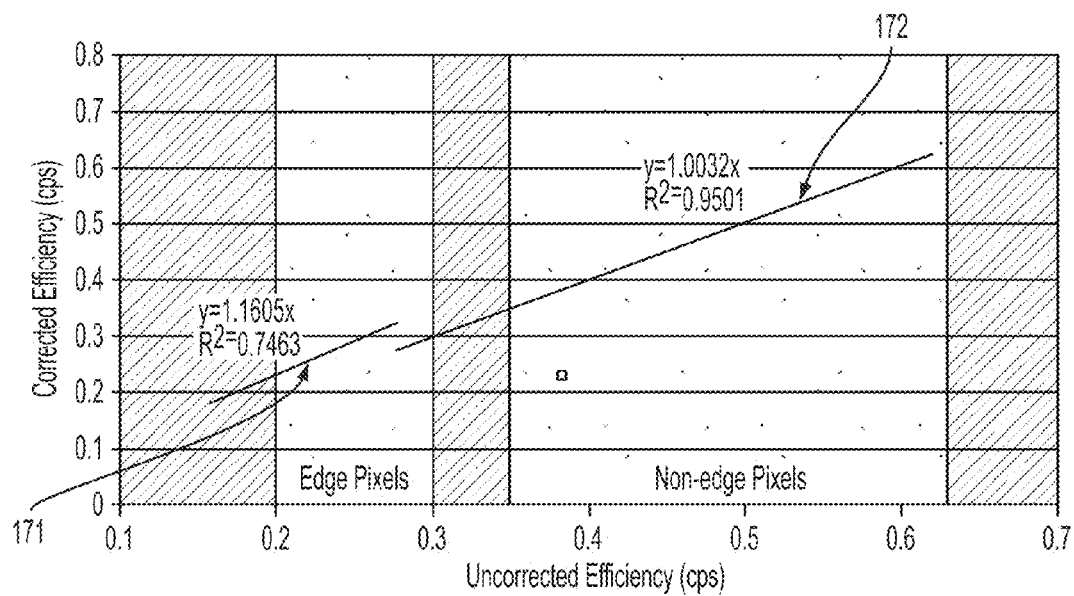
FIG. 17 illustrates lines fitting the scatter plot of FIG. 16.

FIG. 16 illustrates uncorrected vs. corrected signal efficiencies for edge crystals 161 and center crystals 162. In a visual inspection of the two scatter plots 161 and 162, it appears that scatter plot 161 for edge crystals has a slightly greater slope than scatter plot 162. This is confirmed in a computed, best fit graph of the plots in FIG. 17, which illustrates that, in this example, the slope of line 171 is 1.16 ($R^2=0.7462$) while the slope of line 172 is 1 ($R^2=0.95$). This further verifies the approximately 10% improvement in edge crystal sensitivity in the exemplary embodiment.

While embodiments of this disclosure have been depicted, described, and are defined by reference to example embodiments of the disclosure, such references do not imply a limitation on the disclosure, and no such limitation is to be inferred. The subject matter disclosed is capable of considerable modification, alteration, and equivalents in form and function, as will occur to those ordinarily skilled in the pertinent art and having the benefit of this disclosure. For example, while the disclosure focuses on PET applications, a person of ordinary skill in the art could, after reviewing this disclosure, apply the same principles to gamma cameras for SPECT and planar imaging because the systems operate in a similar manner. In addition, other radiation sensors, such as intrinsic solid state sensors, could be substituted for scintillators and photosensors. Other applications include low-dose CT, photon-counting CT, planar imaging, and high-energy physics experiments. The depicted and described embodiments of this disclosure are examples only, and are not exhaustive of the scope of the disclosure.

We claim:

1. A radiation detection device comprising:
a plurality of detector blocks, each detector block comprising a two dimensional array of scintillation crystals;
the plurality of detector blocks being arranged to be adjacent to one another along a particular direction;
a processor configured to receive from a first detector block a first energy signal greater than a predetermined threshold, and in response to receiving said first energy signal, said processor receives a second energy signal from a second detector block adjacent to the first detector block; and
the processor further configured to correct the first energy signal using the second energy signal.

2. The radiation detection device of claim 1, wherein the processor is further configured to correct the first energy signal by summing the first energy signal and the second signal.

3. The radiation detection device of claim 1, wherein the processor is a component of an Event Processing Module that is configured to receive both the first energy signal and the second energy signal.

4. The radiation detection device of claim 1, wherein the plurality of detector blocks are arranged in an axial slot of a detector ring.

5. The radiation detection device of claim 4, wherein the detector ring comprises a plurality of axial slots each including a plurality of detector blocks.

6. The radiation detection device of claim 5, wherein the detector ring is arranged in a PET detector.

7. A method of increasing detection of gamma events at peripheral scintillation crystals of a detector block of a radiation detector device comprising:
detecting from a first detector block a first energy signal greater than a predetermined threshold;
detecting in response to said first energy signal, a second energy signal from a second detector block adjacent to said first detector block; and
correcting the first energy signal using the second energy signal to generate a corrected energy signal.

8. The method according to claim 7, wherein correcting the first energy signal comprises summing the first energy signal and the second energy signal.

9. The method according to claim 7, further comprising receiving the first energy signal and the second energy signal at different Event Processing Modules.

10. The method according to claim 7, further comprising receiving the first energy signal and the second energy signal at the same Event Processing Module.

11. The method according to claim 7, wherein said corrected energy signal represents energy of a first photon of a PET coincidence event, said method further comprising:
detecting from a third detector block a third energy signal greater than a predetermined threshold;
detecting in response to said third energy signal, a fourth energy signal from a fourth detector block adjacent to said third detector block; and
correcting the third energy signal using the fourth energy signal to generate a second corrected energy signal, said second corrected energy signal representing energy of a second photon of said PET coincidence event.

12. A method of increasing crystal efficiency of a radiation detector device having a plurality of detector blocks, comprising:
receiving, from a first detector block comprising a scintillation crystal of a predetermined material, a first signal indicative of first energy of an incident photon;
receiving, from a second detector block comprising a scintillation crystal of the same predetermined material as the first detector block, said second detector block being adjacent to the first detector block, a second signal indicative of second energy of said incident photon;
summing the first signal and the second signal to generate a first corrected signal; and
logging the corrected signal as representative of a photon event if the first corrected signal is above a predetermined threshold.

13. The method according to claim 12, further comprising receiving, from a third detector block, a third signal indicative of energy of a second incident photon;
associating the third signal with the first corrected signal; and
logging a coincidence event if the third signal is above a predetermined threshold.

14. The method according to claim 12, further comprising receiving, from a third detector block, a third signal indicative of first energy of a second incident photon;
receiving, from a fourth detector block, a fourth signal indicative of second energy of the second photon;
correcting the third signal using the fourth signal to generate a second corrected signal;
associating the second corrected signal with the corrected signal; and
logging a coincidence event if the second corrected signal is above a predetermined threshold.

15. The method according to claim 14, wherein the third detector block is adjacent to the fourth detector block.

\* \* \* \* \*